United States Patent [19]

Griffith et al.

[11] Patent Number: 5,407,672

[45] Date of Patent: Apr. 18, 1995

[54] ENHANCING THE ANTI-TUMOR EFFECT OF MELPHALAN WITH L-AMINO ACID OXIDASE

[75] Inventors: Owen W. Griffith, Milwaukee, Wis.; Henry S. Friedman, Durham, N.C.

[73] Assignees: Cornell Research Foundation, Inc., Ithaca, N.Y.; Duke University, Durham, N.C.

[21] Appl. No.: 46,866

[22] Filed: Apr. 8, 1993

[51] Int. Cl.⁶ ............... A61K 37/50; A61K 37/48; A61K 31/195
[52] U.S. Cl. .................. 424/94.4; 424/94.1; 514/564
[58] Field of Search ............... 424/94.4, 94.1; 514/564

[56] References Cited

U.S. PATENT DOCUMENTS 4,772,632  9/1988  Vistica ..................... 514/561
4,997,651  3/1991  Poole et al. ............... 424/422
5,075,108  12/1991  McKenzie et al. .......... 424/85.9

OTHER PUBLICATIONS

Rich, J. N., et al., "Proc. Am. Assoc. Cancer Res.," vol. 34, p. 299, #1778, Mar. 1993, abstract.
Groothuis, D. R., et al., "Cancer Research," vol. 52(20), pp. 5590–5596, Oct. 15, 1992.
Goldenberg, G. J. et al., "Cancer Research," vol. 30(9), pp. 2285–2291, Sep. 1970.
Goldenber, G. J., et al., "Cancer Research," vol. 37, pp. 755–760, Mar. 1977.
Friedman, N. S., et al., "Cancer Research," vol. 48(15), pp. 4189–4195, Aug. 1, 1988.
Friedman, H. S., et al., "Cancer Research," vol. 46(1), pp. 224–228, Jan. 1986.
Friedman, H. S., et al., "Cancer Research," vol. 46(6), pp. 2827–2833, Jun. 1986.
Momma, S., et al., "Proc. of AACR," vol. 26, Mar. 1985, p. 357, #1408 (abstract).
Vistica, D. T., et al., "Proc. of AACR and ASCO," vol. 18, 1977, p. 26, #104 (abstract).
Vistica, D. T., et al., "Cancer Letters," vol. 6, 1979, pp. 345–350.
Wellner, D. et al, Fed. Proc. 31, p. 921, abstract 4019 (1972).
Friedman, H. S., et al, Proceedings of the American Association for Cancer Research, vol. 32, p. 318 Abstract 1886 (Mar. 1991).
The Merck Index, 11th edition, pp. 68 and 914 (1989).
Wellner, D. et al; J. Biol. Chem. 235, 2013–2018 (1960).

*Primary Examiner*—Douglas W. Robinson
*Assistant Examiner*—Kristin Larson

[57] ABSTRACT

L-amino acid oxidase is utilized to reduce plasma level of large neutral amino acids to allow the opportunity of increased melphalan transport into tumors and melphalan is administered when the plasma level of L-amino acid oxidase is sufficiently low so the gain from increased transport outweighs the loss from L-amino acid oxidase-mediated metabolism of melphalan.

8 Claims, 3 Drawing Sheets

ENHANCING THE ANTI-TUMOR EFFECT OF MELPHALAN WITH L-AMINO ACID OXIDASE

This invention was made at least in part with Government support under National Institutes of Health grant number DK 26912. The Government has certain rights in the invention.

TECHNICAL FIELD

This invention is directed at the use of melphalan as an anti-tumor agent.

BACKGROUND OF THE INVENTION

Melphalan, (4-[bis(2-chloroethyl)amino]-L-phenylalanine), is a nitrogen mustard that is useful as a chemotherapeutic agent against many tumors. With cells grown in culture, it is effective against many brain tumors. However, it is poorly transported across the blood brain barrier and thus has not been found effective for use against many brain (intracranial) tumors.

It has been discovered that starving followed by a protein-free diet reduces plasma levels of protein amino acids including large neutral amino acids and increases the blood-to-tumor periphery tissue transfer constant of melphalan both for subcutaneous tumors (representative of all tumors except for brain tumors) and also for brain tumors. See Friedman, H. S., et al, Proceedings of the American Association for Cancer Research, Volume 32, page 318, Abstract 1886, March, 1991. This increase of blood-to-tumor tissue transfer constant might be expected to allow use of lesser dosages of melphalan (and concomitant reduced toxicity) in circumstances where melphalan is now considered useful and the extension of use of melphalan in circumstances now foreclosed by the blood brain barrier, i.e., as an anti-tumor agent against brain (intracranial) tumors. However, the accomplishment of this by means of starving and administration of a protein free diet affords at most limited improvement.

The finding that reduced plasma levels of large neutral amino acids were associated with increased blood-to-tumor melphalan transfer constants is consistent with previous work showing that melphalan is transported by the same transporter as the large neutral amino acids and that the presence of large neutral amino acids in plasma interferes with the transport of melphalan. Thus achieving reduction of plasma levels of large neutral amino acids by means different from or additional to restricted diet to the same or greater degree as is obtained with said restricted diet, should improve melphalan transport and result in a benefit if said different means doesn't concurrently provide deleterious effect.

Various enzymes are known for which large neutral protein amino acids are substrates and which would be useful for reducing plasma levels of these provided they have access to required cosubstrates. However, melphalan is also an amino acid and would likely be a substrate for the same enzymes. Furthermore, the various possible enzymes would be expected to differ in respect to the number of different large neutral amino acids that would be substrates and in their relative kinetic constants vis-a-vis their large neutral amino acid substrates and melphalan. Therefore, such enzymes might be expected, on the one hand, to potentiate the transport of melphalan into tumors by reducing concentrations of plasma large neutral amino acids but on the other hand, would be expected to act in counterproductive fashion by degrading melphalan to an extent which might be larger than the extent of increased melphalan transport from large neural amino acid depletion. Furthermore, each particular enzyme might be expected to have different effects on concentrations of plasma large neutral amino acids and the degradation of melphalan. What is necessary is selection of an enzyme which will reduce plasma large neutral amino acids to enhance melphalan transport but which would be relatively less active toward melphalan or which would be sufficiently inactivated, within the period of reduced plasma amino acid level, so as not to degrade the melphalan to an extent of negating the benefit obtained by enhanced melphalan transport. For any particular enzyme, there is no expectation of success of meeting this criterion.

SUMMARY OF THE INVENTION

It has been discovered herein that L-amino acid oxidase meets this criterion and successfully enhances the delivery of melphalan to obtain improved effect at conventional melphalan dosages in treatment of subcutaneous tumors, and to provide enhanced transport of melphalan across the blood brain barrier to obtain improved anti-tumor effect against brain tumors, and when accompanied by fasting and/or a protein restricted diet provides improved efficacy over fasting and protein restricted diet alone. In contrast to starving which reduces the plasma level of essentially all amino acids, use of L-amino acid oxidase reduces the plasma level of only amino acids that are actively degraded by L-amino acid oxidase, namely, plasma large neutral amino acids as defined hereinafter and provides α-ketoacid reaction products which are eventually converted back to amino acids in the body or are catabolized intracellularly for energy.

It has been discovered herein that improved anti-tumor effect is obtained by utilizing L-amino acid oxidase to reduce plasma level of large neutral protein amino acids to allow the opportunity of increased melphalan transport into tumors and then capitalizing on this opportunity by administering melphalan when the plasma level of L-amino acid oxidase activity is sufficiently low so the gain from increased transport outweighs the loss from L-amino acid oxidase-mediated metabolism of melphalan.

The method herein is directed to treating a subject (human patient or animal) for tumors and comprises the steps of (a) administering L-amino acid oxidase to said subject at a dosage ranging from about 1 to about 100 units/ml of plasma (corresponding to about 85 to about 8500 units/kg of body weight), which is non-toxic and which is sufficient to reduce plasma level of large neutral amino acids from a normal level to a melphalan transport improving level;

(b) administering melphalan in an anti-tumor effective amount to the subject wherein plasma level of large neutral amino acids remains reduced from normal level within about 2 to 36 hours after administering in step (a), so as to improve the transport of the melphalan into the tumors, as evidenced by increase in number of subjects surviving past control or increased median survival time of subjects compared to when melphalan is administered without L-amino acid oxidase being administered first.

In a preferred method, the L-amino acid oxidase is administered in step (a) at a dosage ranging from about 10 units/ml to about 50 units/ml and the administration of step (b) is carried out from 12 to 30 hours after the administration of step (a).

In a very preferred embodiment, the method herein comprises preventing replenishment of large neutral amino acids to plasma during the period between the administration of step (a) and the administration of step (b) and optimally also during the period of melphalan uptake into tumors by causing the patient to fast or by administering a protein-free diet or by causing the patient to fast followed by administering a protein-free diet.

One unit of L-amino acid oxidase is that amount which converts 1 μmol of L-leucine to α-ketoacid reaction product per minute at 37° C. and corresponds approximately to 0.01 mg of crystalline L-amino acid oxidase.

The term "large neutral amino acids" is used herein to mean the group of amino acids consisting of leucine, methionine, phenylalanine, tryptophan and tyrosine.

The term "normal level" of large neutral amino acids is used herein to mean the concentration of each of the large neutral amino acids found in a subject (patient or animal) not experiencing dietary restriction or supplementation.

The term "melphalan transport improving level" is used herein to mean a concentration of the large neutral amino acids in a subject (patient or animal) that allows melphalan transport into the tumor to be improved relative to the extent of melphalan transport into the tumor that would be observed in the absence of L-amino acid oxidase and large neutral amino acid depletion.

Amino acids can be qualified using standard techniques on a model 7300 amino acid analyzer (Beckman Instruments, Inc., Palo Alto, Calif.).

DETAILED DESCRIPTION OF THE INVENTION

Figure 1:
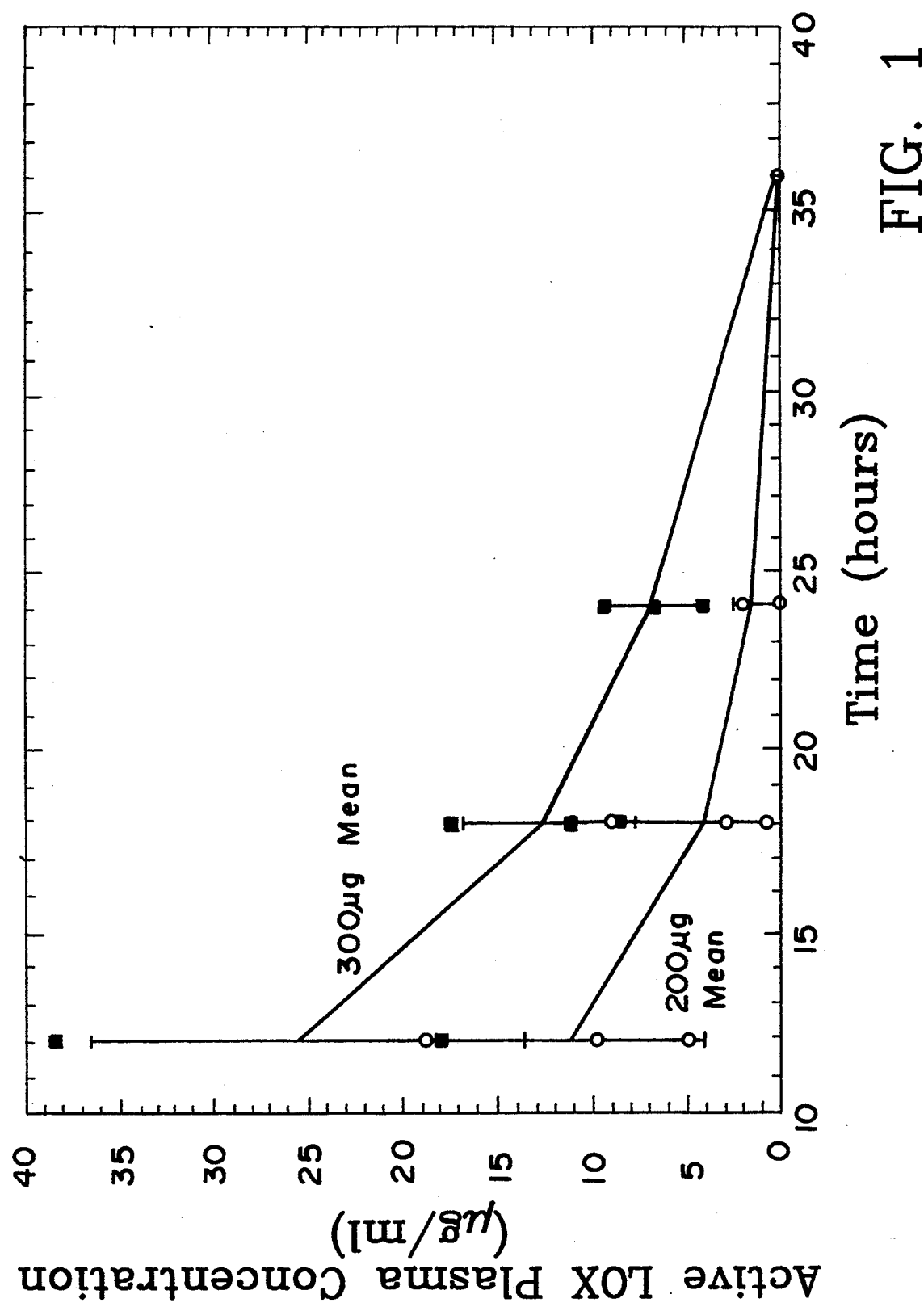
FIG. 1 depicts graphs of L-amino acid oxidase plasma concentration (denoted "Active LOX Plasma Concentration") vs. time after intravenous treatment of mice with 200 and 300 μg of L-amino acid oxidase, based on data determined in Example II.

L-amino acid oxidase is a flavoprotein that catalyzes the oxidative deamination of certain L-amino acids to the corresponding α-keto acids. It occurs in many snake venoms (e.g., the venom of the Eastern Diamondback rattlesnake) and is isolated therefrom as described in Wellner, D., et al, J. Biol. Chem. 235,2013 (1960). For its use in the method herein, the L-amino acid oxidase should be pure, i.e., free of all of the toxins and other enzymes present in the snake venom from which it is isolated. The required purification is accomplished, for example, by isolating the compound in crystallized form by dissolving 1 gm lyophilized snake venom (Miami Serpentarium) in 100 ml water, adding 10 ml of 100 mM L-leucine, heating under $N_2$ to 70° C. for 5 minutes, centrifuging to remove precipitated protein, mixing the supernatant solution with 400 mg (dry weight) of hydroxyapatite gel, adding HCl to reduce the pH to 5.5, centrifuging to obtain a precipitate of enzyme bound to gel, resuspending the precipitate in 35 ml of 2.3M ammonium sulfate in 80 mM Na acetate buffer, pH 4.6, to release the enzyme from the gel, centrifuging to obtain a supernatant containing enzyme, adding 141 mg/ml of ammonium sulfate to precipitate the enzyme, centrifuging to obtain a pellet of the precipitate, dissolving the pellet in cold water, dialyzing the resulting solution against water at 4° C. to cause crystallization of the L-amino acid oxidase, collecting the crystals by centrifugation, redissolving in 2 ml 100 mM KCl, again dialyzing against water to form crystals and then recrystallizing again. The crystals can be dissolved in physiological saline to give an injectable preparation.

As indicated above, the L-amino acid oxidase is administered at a dosage ranging from about 1 to about 100 units/ml of plasma (corresponding to about 85 to about 8500 units/kg of body weight) which is non-toxic and which is sufficient to reduce plasma level of large neutral amino acids from a normal level to a melphalan transport improving level. The dosage for the L-amino acid oxidase can range, for example, from about 5 to about 25 units/ml of plasma (corresponding to about 425 to about 2125 units/kg of body weight) to reduce plasma level of large neutral amino acids in a patient to a melphalan transport improving level of less than 50% of normal level, and from about 10 to about 50 units/ml of plasma (corresponding to about 850 to about 4250 units/kg of body weight) to reduce plasma level of large neutral amino acids in a patient to a melphalan transport improving level of less than 10% of normal level.

The L-amino acid oxidase can be administered by any parenteral route, e.g., intravenously, intraperitoneally or subcutaneously. A preferred method of administration is intravenous administration.

The L-amino acid oxidase can also be administered to the patient by attaching it to an extracorporeal reactor and passing the patient's blood through the reactor. Said reactor can be a packed bed of Dacron fibers to which L-amino acid oxidase is attached using γ-aminopropyltriethoxysilane and glutaraldehyde (general method of R. Y. C. Ko, et al, J. Biomed. Res., 10, 249-258(1976)) or said reactor may be an insoluble carrier matrix of reconstituted bovine collagen containing L-amino acid oxidase (general method of L. S. Olanoff, et al, J. Biomed. Res., 8, 125-136(1977)) or said reactor may be a conventional hollow-fiber hemodialyzer to which L-amino acid oxidase is attached covalently (general method of J. A. Jackson, et al, J. Pharmacol. Expt. Ther., 209, 271-274(1979)). In each case the patient's blood is passed through the extracorporeal reactor by means of conventional arteriovenous cannulation wherein blood is removed from the patient through an arterial cannula, passed through the extracorporeal reactor and then returned to the patient through a venous cannula. Use of an extracorporeal reactor as described above, and disconnecting it prior to melphalan administration, eliminates the opportunity for L-amino acid oxidase to degrade melphalan.

The L-amino acid oxidase is also advantageously administered in methoxypropylene glycol (PEG) modified form, to increase its plasma half-life and to decrease its antigenicity. The PEG utilized is preferably of 5000 daltons. The L-amino acid oxidase and PEG are covalently coupled using 2,4,6-trichloro-s-triazine (general method of K. V. Savoca, et al, Biochem. Biophys. Acta, 578, 47-53(1979)) and PEG is attached to 50% to 60% of the free amino groups of L-amino acid oxidase. L-amino acid oxidase modified in this manner has a circulating half-life more than 10-fold that of unmodified L-amino acid oxidase. The term "utilizing L-amino acid oxidase" used herein includes using unmodified L-amino acid oxidase as well as using PEG-modified L-amino acid oxidase.

Turning now to step (b), as indicated above the dosage of melphalan administered is an anti-tumor effective amount. Normally, this ranges from about 2 to about 120 mg/kg of body weight (corresponding to about 6 to about 360 mg/square meter of body surface). Preferably, this ranges from about 5 to about 70 mg/kg of body weight (corresponding to about 15 to about 210 mg/square meter of body surface), very preferably from about 11.8 to about 23.7 mg/kg (corresponding to about 35.5 to about 71 mg/square meter of body surface).

As indicated above, administration in step (b) is carried out when the plasma level of large neutral amino acids remains reduced from normal level so as to improve the transport of the melphalan into the tumors. When L-amino acid oxidase is administered parenterally in unmodified form, the administration of step (b) is ordinarily carried out from 2 to 36 hours, very preferably from 12 to 30 hours, after the administration of step (a). When the embodiment is used where L-amino acid oxidase is linked to an extracorporeal reactor, L-amino acid oxidase mediated degradation of melphalan is not a factor and therefore time need not be provided for L-amino acid oxidase inactivation to a level where it will not degrade melphalan to too great an extent; in this case melphalan is preferably administered at the earlier times in the above range. When the embodiment is used where the L-amino acid oxidase is administered in PEG-modified form, the period for melphalan administration can be shifted to accommodate for the increased effective life of the L-amino acid oxidase, e.g., to range from 12 to 360 hours after administration of L-amino acid oxidase, with melphalan given, in some cases, more than once during that interval.

Preferably the melphalan is administered in an anti-tumor effective amount to the patient wherein the plasma large neutral amino acids are at the reduced level, when the patient's plasma L-amino oxidase level is such that less than 15% of the melphalan would be metabolized by the L-amino acid oxidase during the period in which melphalan uptake into the tumors is at least 85% complete. Very preferably, the melphalan is administered when the patient's plasma L-amino acid oxidase level is such that less than 10% of the melphalan would be metabolized by the L-amino acid oxidase during the period in which melphalan uptake into the tumors is at least 90% complete. The period during which the patient's plasma level is such that metabolizing of melphalan is restricted to the recited degree and melphalan uptake into tumors is complete to the recited degree, may be estimated from data on L-amino acid oxidase concentration in plasma versus time after administration, data on the rate of melphalan degradation at any L-amino acid oxidase plasma concentration coupled with the assumption that L-amino acid oxidase mediated melphalan degradation is expected to be directly proportional to the L-amino acid oxidase concentration and data known from clinical studies on the time required for uptake of melphalan into various kinds of tumors to the specified amount of completeness modified by the estimate of reduction of the time as a result of the L-amino acid oxidase treatment.

Conventionally melphalan is administered orally. This is a suitable method of administration herein and is a preferred method of administration when the embodiment relying on PEG-modified L-amino acid oxidase is utilized. However, when L-amino acid oxidase in unmodified form is administered parenterally or is administered via an extracorporeal reactor, the melphalan is preferably administered parenterally, very preferably intravenously as a bolus injection.

We turn now to the embodiment where replenishment of large neutral amino acids to plasma is prevented during the period between the administration of step (a) and the administration of step (b). This can be carried out, for example, by precluding the patient from intake of nutriments providing large neutral amino acids to the plasma essentially all during the period between the administering of step (a) and the administering of step (b), e.g., by causing the patient to fast or by administering a protein-free or protein-restricted diet during said period. Suitable protein-free or protein-restricted diets include, for example, standard total parenteral nutrition solutions formulated to contain no amino acids or to contain no large neutral amino acids, protein-free liquids (e.g., water, soda, coffee), and oral diets containing only carbohydrates and fats. In a preferred embodiment, the patient is caused to fast for 15 to 20 hours after the administration of step (a) and the fasting is followed by administration of protein-free diet (e.g., amino acid-free total parenteral nutrition solutions or other alternatives recited hereinbefore) for 4 to 8 hours with the latter providing sustainment for the subsequent melphalan administration and to mitigate sickness being caused by the fasting, and very preferably, the protein-free diet is continued for up to 4 hours after melphalan administration so the plasma large neutral amino acids are not replenished prior to the uptake of the melphalan.

The invention is illustrated in the following examples:

EXAMPLE I

The kinetic constants $K_m$, $V_{max}$, and $(V_{max})/(K_m)$ for L-amino acid oxidase with various amino acid substrates were determined, where $K_m$ stands for the concentration in mM of substrate required for reaction at a rate of 0.5 $V_{max}$ and $V_{max}$ is the maximum rate of product formation achieved per mg of L-amino oxidase as the concentration of substrate approaches infinity, and $(V_{max})/(K_m)$ is the best measure of L-amino acid oxidase activity toward a substrate. $K_m$ and $V_{max}$ were determined by plotting 1/rate vs. 1/[substrate] to give a line which intersects the Y-axis at $1/V_{max}$ and intersects the X-axis at $-1/K_m$. The reaction mixtures utilized contained in a final volume of 1.0 ml, the following: 100 mM glycylglycine buffer, pH 7.5, 0.3 mM NADH, 2 mM α-ketoglutarate, 0.5 mM ADP, 20 I.U. glutamate dehydrogenase (Sigma Chemicals, St. Louis, Mo.), and L-amino acid substrate or melphalan at concentrations ranging from 0.1 to 16 mM. The temperature was 37° C. In this system L-amino acid oxidase converted L-amino acid or melphalan to the corresponding α-keto acid and ammonia; ammonia then reacted stoichiometrically with α-ketoglutarate and NADH in a reaction catalyzed by glutamate dehydrogenase to give NAD+ and glutamate. The oxidation of NADH to NAD+ is accompanied by a decrease in $OD_{340}$, which was monitored and used to determine the amount of ammonia made available for reaction (1 mM NADH converted to NAD+ causes a $\Delta OD_{340}$ of 6.2 in the 1 cm cuvettes used).

The data is set forth in Table 1 below:

TABLE 1

| Substrate | $K_m$ (mM) | $V_{max}$ (μmol/min · mg) | $(V_{max})/(K_m)$ |
|---|---|---|---|
| L-Alanine | N/A | 0 | 0 |
| L-Leucine | 0.6 | 100 | 167 |
| L-Isoleucine | 2.05 | 33 | 16 |
| L-Valine | 19 | 13 | 0.7 |
| L-Methionine | 0.47 | 70 | 150 |
| L-Phenylalanine | 0.13 | 33 | 261 |
| L-Tryptophan | 0.22 | 43 | 194 |
| L-Tyrosine | 0.13 | 37 | 295 |
| Melphalan | 0.30 | 11 | 37 |

The data provides a screening test indicating that L-amino acid oxidase has potential in vivo for reducing the level of the large neutral amino acids L-leucine, L-methionine, L-phenylalanine, L-tryptophan and L-tyrosine without unduly degrading melphalan or other amino acids.

EXAMPLE II

Mice (20–25 gm) were administered either 300 μg or 200 μg of pure L-amino acid oxidase by intravenous injection. At 12, 18, 24 and 36 hours after administration, the L-amino acid oxidase activity of the plasma was determined.

L-amino acid oxidase activity was determined as follows: Blood was obtained from the heart in a heparinized syringe. After centrifugation (10,000×g) for 30 seconds, plasma was obtained as the supernatant. Then assay reaction mixtures were made up (100 μl final volume) containing 400 mM Tris HCl buffer, pH 7.5, 1 mM L-[$^{14}$C]leucine (0.08 μCi) and 40 μl plasma. The reaction mixtures were incubated for 10 min. at 37° C. The reaction was stopped by addition of 100 μl of 20% trichloroacetic acid and the vials were placed on ice for five min. The reaction mixtures were then centrifuged for 1 min. to sediment precipitated protein, and 180 μl of supernatant was loaded onto a small column (0.5×2.5 cm) of Dowex 50W X 8 (200–400 mesh) cation exchange resin (H+-form). The columns were washed with 3.8 ml of water, and the effluent which contains α-keto-[$^{14}$C]isocaproic acid, the product of L-amino acid oxidase activity on leucine, was collected in a test tube and mixed. Radioactivity in two ml of the mixed effluent was determined by liquid scintillation counting. The amount of product formed (nmol/min) is determined from the known specific activity of the L-[$^{14}$C]leucine used. The amount of L-amino acid oxidase is calculated by knowing that 1 μg of enzyme forms 100 nmol product/min under these conditions.

Since mice of the size used have about 2 ml of blood and 1.2 ml of plasma, the peak plasma concentration of L-amino acid oxidase is calculated to be about 250 and 167 μg/ml in the mice given 300 and 200 μg of L-amino acid oxidase, respectively. These peak concentrations would occur immediately following injection.

The results as determined at 12, 18, 24 and 36 hours are shown in FIG. 1 wherein the open circles denote results on administration of 200 μg of L-amino acid oxidase and the filled in squares denote results on administration of 300 μg of L-amino acid oxidase. The graphs are defined by points representing the mean ±S.D. for data for 3 mice. As indicated in FIG. 1, L-amino acid oxidase activity on plasma decreases with time after 12 hr. but persists for at least 24 hours. By 36 hr., activity was essentially zero.

Plasma large neutral amino acids were determined at the 12, 18 and 24 hours after L-amino acid oxidase administration.

Results for 300 μg intraperitoneal administration of L-amino acid oxidase are set forth in Table 2 below wherein "control" is amino acid level in mice where L-amino acid oxidase was not administered. Concentrations are given as μM.

TABLE 2

| Amino Acid | Control | 6 hr | 24 hr | 36 hr | 48 hr |
|---|---|---|---|---|---|
| Leucine | 222 | 121 | 168 | 234 | 180 |
| Methionine | 97 | 56 | 67 | 106 | 106 |
| Phenylalanine | 95 | 62 | 46 | 78 | 70 |
| Tryptophan | 70 | 54 | 48 | 62 | 92 |
| Tyrosine | 133 | 71 | 42 | 63 | 87 |

The above data suggests that plasma large neutral amino acids can be efficiently depleted at the injected dose between 6 and 24 hr administration. In the period from 24 to 36 hours, the remaining activity is adequate to maintain plasma levels of some large neutral amino acids at a low level. The dose used is not so high that melphalan itself would be degraded rapidly.

EXAMPLE III

Mice (20–30 gm) were administered either 100 μg, 200 μg, 300 μg or 400 μg of L-amino acid oxidase by intravenous injection.

Figure 2:
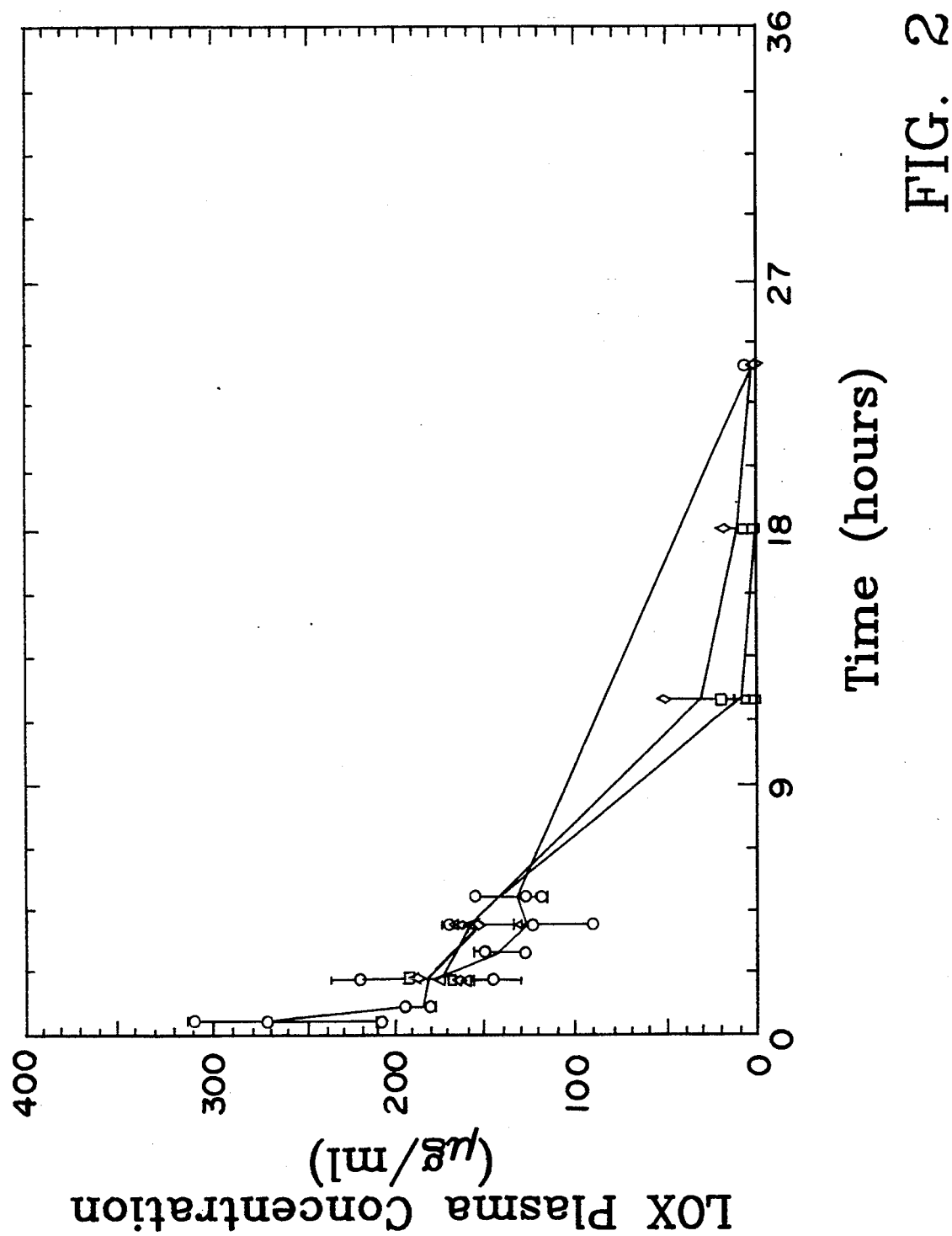
FIG. 2 depicts graphs of L-amino acid oxidase plasma concentration (denoted "LOX plasma concentration") vs. time after intravenous treatment of mice with various doses of L-amino acid oxidase, showing plasma L-amino oxidase activity at denoted intervals after acid oxidase treatment, based on data determined in Example III.

Plasma L-amino oxidase activity was determined at intervals thereafter as shown in FIG. 2 wherein the filled in circles denote results on administration of 100 μg, the filled in squares denote results on administration of 200 μg, the filled in diamonds denote results on administration of 300 μg, and the filled in triangles denote results on administration of 400 μg.

The graphs are defined by points representing the mean ±S.D. for 3 mice.

As shown in FIG. 2, the plasma L-amino oxidase concentration was greater than 50 μg/ml at all times up to 9 hours.

The large neutral amino acid levels corresponding to the L-amino oxidase levels of FIG. 2 are given in Table 3 below:

TABLE 3

| | | Plasma Amino Acids | | | | |
|---|---|---|---|---|---|---|
| Time (hr) | Dose (units) | Leucine (μM) | Isoleucine (μm) | Methionine (μM) | Phenylalanine (μM) | Tyrosine (μM) |
| 0 | — | 244 ± 73 | 150 ± 42 | 125 ± 39 | 144 ± 40 | 165 ± 64 |
| 0.5 | 2 | 42 ± 6 | 103 ± 7 | 28 ± 3 | 10 ± 0 | 5 ± 0 |
| 1 | 2 | 75 ± 22 | 110 ± 11 | 42 ± 16 | 13 ± 9 | 7 ± 3 |
| 2 | 2 | 26 ± 6 | 86 ± 3 | 22 ± 4 | 5 ± 0 | 5 ± 0 |

TABLE 3-continued

| Time (hr) | Dose (units) | Plasma Amino Acids | | | | |
|---|---|---|---|---|---|---|
| | | Leucine (μM) | Isoleucine (μm) | Methionine (μM) | Phenylalanine (μM) | Tyrosine (μM) |
| 3 | 2 | 101 ± 62 | 125 ± 26 | 38 ± 20 | 22 ± 25 | 13 ± 13 |
| 4 | 2 | 148 ± 21 | 144 ± 9 | 65 ± 17 | 40 ± 11 | 27 ± 6 |
| 5 | 2 | 51 ± 26 | 100 ± 26 | 22 ± 5 | 8 ± 3 | 5 ± 0 |
| 24 | 2 | 253 ± 16 | 165 ± 4 | 108 ± 12 | 112 ± 25 | 90 ± 33 |
| 2 | 4 | 13 ± 11 | 86 ± 18 | 28 ± 14 | 5 ± 0 | 5 ± 0 |
| 4 | 4 | 23 ± 9 | 98 ± 12 | 18 ± 1 | 5 ± 0 | 5 ± 0 |
| 12 | 4 | 152 ± 52 | 90 ± 30 | 76 ± 18 | 55 ± 16 | 64 ± 41 |
| 18 | 4 | 165 ± 13 | 96 ± 10 | 80 ± 11 | 60 ± 3 | 46 ± 2 |
| 24 | 4 | 159 ± 41 | 93 ± 22 | 66 ± 19 | 65 ± 13 | 53 ± 11 |
| 36 | 4 | 151 ± 11 | 83 ± 10 | 49 ± 1 | 63 ± 2 | 55 ± 3 |
| 2 | 6 | 5 ± 0 | 45 ± 6 | 18 ± 1 | 5 ± 0 | 5 ± 0 |
| 4 | 6 | 5 ± 0 | 51 ± 14 | 16 ± 3 | 5 ± 0 | 5 ± 0 |
| 12 | 6 | 153 ± 32 | 95 ± 27 | 72 ± 14 | 55 ± 6 | 48 ± 8 |
| 18 | 6 | 157 ± 14 | 97 ± 6 | 81 ± 13 | 51 ± 5 | 37 ± 8 |
| 24 | 6 | 101 ± 26 | 61 ± 13 | 54 ± 13 | 46 ± 12 | 40 ± 5 |
| 36 | 6 | 164 ± 44 | 88 ± 20 | 58 ± 20 | 65 ± 7 | 78 ± 40 |
| 2 | 8 | 5 ± 0 | 42 ± 8 | 13 ± 5 | 5 ± 0 | 5 ± 0 |
| 4 | 8 | 5 ± 0 | 56 ± 17 | 14 ± 3 | 5 ± 0 | 5 ± 0 |

As indicated in Table 3, the concentration of large neutral amino acids during 30 minutes to 5 hours after administration is reduced to a very low level thereby providing high melphalan transfer constants for plasma to tumor tissue transfer. While melphalan administered in the first 6 hours following L-amino acid oxidase administration will be partially degraded by the high levels of L-amino acid oxidase present, in some cases the L-amino acid oxidase mediated decrease in plasma amino acids can cause an increase in tumor uptake of melphalan that more than compensates for the L-amino acid oxidase mediated partial degradation of melphalan.

EXAMPLE IV

Melphalan was allowed to react with L-amino acid oxidase in a reaction mixture (final volume, 100 μl) containing phosphate buffered saline, pH 7.4, 50 μM [$^{14}$C]melphalan and 125 μg/ml (12.5 units/ml) L-amino acid oxidase. At 5, 15 and 30 minutes after formation of the reaction mixture, 10 μl aliquots were removed and fractionated by HPLC.

The HPLC was carried out on a Brownlee C18 reverse phase column under the following conditions: Solvent, 0.1M ammonium acetate, pH 4.1, with 79% methanol; flow rate 1 ml/min for 15 min, then 1.5 ml/min; fractions of 1 min collected and radioactivity determined by liquid scintillation counting.

The HPLC eluant was analyzed for radioactivity and peaks associated with melphalan (elution time, 8–9 min), or its reaction products (products I and II eluting at 10–12 and 23.5–25 min, respectively) were determined. The control incubation contained no L-amino acid oxidase, but was analyzed similarly. Product I is believed to be ketomelphalan, i.e., 4-[bis(2-chloroethyl)amino]-phenylacetate.

Figure 3:
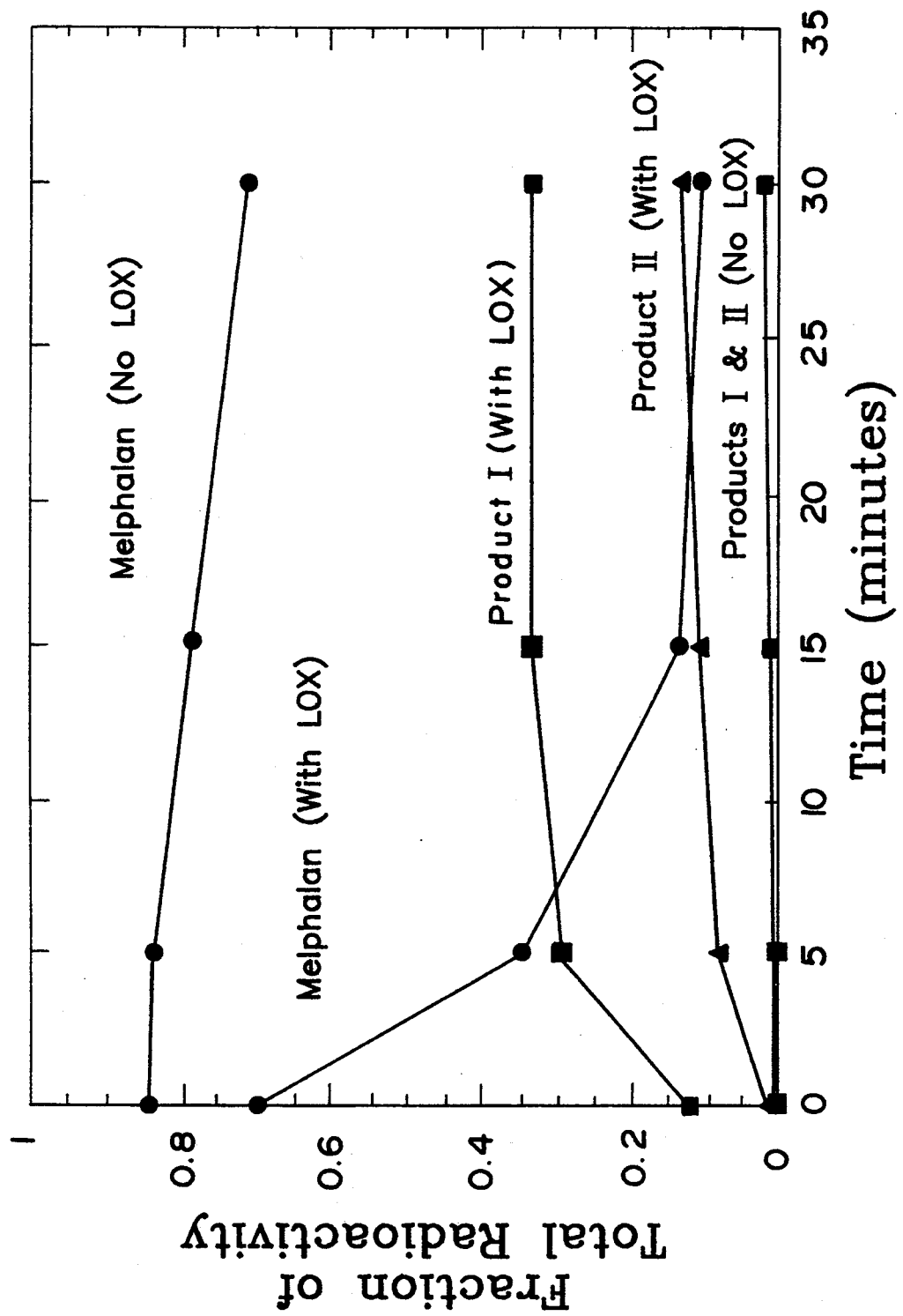
FIG. 3 depicts graphs of fraction of total radioactivity versus time, based on data determined in Example IV directed to HPLC determination of melphalan (50 μM) reaction with L-amino acid oxidase (0.25 mg/ml) and a control with no L-amino acid oxidase.

The results are shown in FIG. 3 wherein LOX stands for L-amino acid oxidase.

As shown in FIG. 3., melphalan showed good stability for at least 30 minutes in the absence of L-amino oxidase and in the presence of L-amino acid oxidase at 12.5 units/ml was degraded at an initial rate of 50% reaction in 5 minutes.

In this concentration range, the rate of L-amino acid oxidase mediated melphalan degradation is expected to be essentially directly proportional to the L-amino acid oxidase concentration. Thus, at a plasma L-amino acid oxidase concentration of 1.25 units/ml, melphalan is expected to be degraded with a period required for 50% reaction of 50 minutes, and at a plasma concentration of 0.25 units/ml, melphalan is expected to be degraded with a period required for 50% reaction of 250 minutes. As shown in FIG. 1, L-amino acid oxidase concentrations are 1.25 units/ml (12.5 μg/ml) or less 12 to 15 hours following 200 to 300 μg L-amino acid oxidase administration. In particular, as indicated from FIG. 1, melphalan is expected to be degraded with a period required for 50% reaction ranging from 50 to 250 minutes when administered 12 to about 30 hours after L-amino acid oxidase administration at the concentrations of L-amino acid oxidase administered in Example II. Studies in man have indicated that the disappearance of most melphalan from plasma is 50% complete after 7.7 minutes. This uptake would be expected to be increased with the plasma large neutral amino acid reduction provided by L-amino acid oxidase. Thus uptake of melphalan into brain tumors would be more than 50% complete, 75% complete and 87.5% complete 7.7 min, 15.4 min and 23.1 min following injection, i.e. within the period indicated for 50% melphalan reaction.

The above provides a rational basis for estimating the appropriate time following L-amino acid oxidase administration, to administer melphalan. Each tumor type will have its characteristic affinity for melphalan. Thus for a tumor type where uptake is relatively fast (50% uptake in 30 minutes or less), uptake will be greater than 87% complete in 90 minutes. At a plasma concentration of 5 μg/ml (melphalan administration about 18 hrs after 167 μg/ml L-amino oxidase injection or about 30 hrs after 250 μg/ml injection), less than 25% of the melphalan would be metabolized by the L-amino acid oxidase in 90 minutes (time required for 50% reaction of 250 min, k=0.00276 min) in the absence of melphalan uptake. Considering that melphalan was taken up into tumors simultaneously with L-amino acid oxidase mediated metabolism, the loss of melphalan is expected to be less than 10%. Since L-amino acid oxidase mediated removal of plasma large neutral amino acids will improve melphalan uptake by more than 10%, the small loss of melphalan due to L-amino acid oxidase mediated metabolism can be considered insignificant provided the L-amino acid oxidase dose and timing of the melphalan injection are properly adjusted.

EXAMPLE V

Mice (20–25 gm) were given melphalan and/or L-amino acid oxidase by intraperitoneal injection. Melphalan was administered at 1.0 or 0.5 times the previously established $LD_{10}$ dose (dose where 10% die), namely 11.8 and 23.7 μmole/kg body weight, respectively. Highly purified L-amino oxidase was given at a dose of 100 μg or 400 μg per mouse in two separate experiments. Results for the first experiment are shown in the first five entries in Table 4 below. "LOX" means L-amino acid oxidase:

TABLE 4

| Treatment | Mean Nadir weight loss (g) | Mean Nadir Percentage Weight Loss (%) | Deaths |
|---|---|---|---|
| 1.0 $LD_{10}$ Melphalan | 9.2 | 31.8 | 0/6 |
| 0.5 $LD_{10}$ Melphalan | 4.2 | 16.6 | 0/6 |
| 100 μg LOX | 0.3 | 1.1 | 0/6 |
| 100 μg LOX & 1.0 $LD_{10}$ Melphalan | 5.8 | 19.8 | 0/6 |
| 100 μg LOX & 0.5 $LD_{10}$ Melphalan | 4.7 | 16.3 | 0/6 |
| 1.0 $LD_{10}$ Melphalan | 4.3 | 14.6 | 0/6 |
| 400 μg LOX | 0.0 | 0.0 | 0/6 |
| 400 μg LOX & 1.0 $LD_{10}$ Melphalan | 3.0 | 12.5 | 2/6 |

As shown in Table 4, melphalan alone at either dose caused significant weight loss but no deaths in 6 mice; L-amino acid oxidase alone at either dose caused no deaths and no significant weight loss in the mice; at the lower dose of L-amino acid oxidase, melphalan plus L-amino acid oxidase caused significant weight loss but no deaths in 6 mice; at the highest doses, melphalan plus L-amino acid oxidase resulted in the death of 2 of 6 mice but weight loss was not greater than with melphalan alone. Overall, the results indicate that L-amino acid oxidase does not significantly increase the toxicity of melphalan at 1.0 or 0.5 times its $LD_{10}$ dose. The difference between the results for "1.0 $LD_{10}$ Melphalan" in the two experiments in Table 4 may be explained by the biological variability which is always seen in these types of experiments.

EXAMPLE VI

Subcutaneous D-54 MG tumors (a human glioma-derived continuous cell line), grown in athymic BALB/C mice were excised and mechanically homogenized in zinc option medium as described in Bullard, D. E., J. Neuropath. Exp. Neurol. 40:410–427, 1981. The homogenate was mixed with an equal amount of 1% methylcellulose and 10 μl of homogenate (about $10^5$ tumor cells) injected into the right frontal hemisphere of athymic mice (20–25 gm) for brain, i.e., intracranial (IC) tumors and 50 μl of homogenate was injected subcutaneously into the right flank for subcutaneous (SC) tumors.

The effects on tumor growth and animal survival of melphalan and L-amino acid oxidase, alone and in combination were determined in groups of mice previously injected intracranially or subcutaneously with tumor cell line as described above.

L-amino acid oxidase was administered at a dose of 100 μg (83 μg/ml in plasma) or a dose of 400 μg (333 μg/ml in plasma) by intravenous injection 8 days after injection of tumor cells. Melphalan when used alone was administered at a dose of 0.5 times or 1.0 times its $LD_{10}$ dose by intraperitoneal injection 8 days after injection of tumor cells. Melphalan when used in combination with L-amino acid oxidase was administered intraperitoneally 2 hours after L-amino acid oxidase injection.

The results are shown in Table 5 below wherein LOX means "L-amino acid oxidase", MDTD means "mean days to death", T-C means growth delay to 5 times pretreatment volume for treated tumors minus growth delay to 5 times pretreatment volume for untreated tumors and regressions means percentage of mice where tumors became smaller.

TABLE 5

| Treatment | Intracranial D54 MG | | Subcutaneous D54 MG | |
|---|---|---|---|---|
| | MDTD | Long Term Survivors | T-C | Regressions (%) |
| No Treatment | 19.5 | 0/10 | 0 | 0/10 (0%) |
| LOX (100 μg i.v.) | 22.0 | 0/10 | 0.2 | 0/10 (0%) |
| Melphalan (0.5 $LD_{10}$) | 26.5 | 0/10 | 7.2 | 2/10 (20%) |
| Melphalan (0.5 $LD_{10}$) & LOX (100 μg i.v.) | 27.0 | 0/10 | 8.9 | 5/10 (50%) |
| Melphalan (1.0 $LD_{10}$) | 34.0 | 0/10 | 13.3 | 6/10 (50%) |
| Melphalan (1.0 $LD_{10}$) & LOX (100 μg i.v.) | 33.0 | 0/10 | 14.6 | 5/8 (63%) |

As shown in Table 5, L-amino acid oxidase (LOX) alone had little effect on the growth of either intracranial (IC) or subcutaneous (SC) tumors. Melphalan alone at a dose of 0.5 times the $LD_{10}$ dose caused a 7.0 day increase in median survival time of mice with intracranial tumors compared to untreated control and a 7.2 day growth delay with two regressions in 10 mice with subcutaneous tumors. Administration of L-amino acid oxidase with this dose of melphalan increased median survival time to 7.5 days over untreated control for intracranial tumors and increased the growth delay to 5 times pretreatment volume to 8.9 days, with 5 regressions in 10 mice. At a higher dose of melphalan (1.0 times the $LD_{10}$ dose), the administration of L-amino acid oxidase did not improve the response of intracranial tumors but did improve the response of subcutaneous tumors.

Example VII

Intracranial (IC) D-54 MG tumors were grown in Balb/C mice as described in Example VI. Treatment groups were None (Control), Melphalan alone, Melphalan+diet, Melphalan+LOX, and Melphalan+diet+LOX ("LOX" is used to mean L-amino acid oxidase). L-amino acid oxidase was administered intravenously at a dose of 300 μg per mouse. Melphalan was administered intraperitoneally at a dose of 1.0 times its $LD_{10}$ (the dose previously determined to kill 10% of the animals when used alone). Animals were carefully monitored to determine "days to death." Scheduling for the treatment groups was as follows: Mice in the "None (Control)" group received no treatment and the "days to death", therefore represent survival in days after implantation of the intercranial tumors. Animals in the "Melphalan alone" group received melphalan 6 days after tumor implantation and the "days to death" values indicate days of survival after tumor implantation. Animals in the "Melphalan+diet" group were fasted for 18 hours beginning 5 days after tumor implantation and were then allowed free access to a protein-free diet (Bio-Serv Inc. catalogue #F2247) for 6 hours after the fast; at that time melphalan was administered, and the animals were allowed a further 2 hours access to the protein-free diet. Animals were then returned to cages with conventional diet and were monitored for survival; "days to death" indicates survival in days following tumor implantation. Animals in the "Melphalan+-LOX" group received 300 μg of L-amino acid oxidase 5 days after tumor implantation and 24 hours after L-amino acid oxidase administration were given melphalan. "Days to death" indicates survival in days after tumor implantation. Animals in the "Melphalan+-diet+LOX" group received 300 μg of L-amino acid oxidase 5 days after tumor implantation and were fasted for 18 hours after L-amino acid oxidase administration. Animals were then allowed access to a protein-free diet (Bio-Serv Inc. Catalogue #F2247) for 6 hours and were injected with melphalan 24 hours after L-amino acid oxidase administration. Access to the protein-free diet was continued for 2 hours after melphalan administration, and the animals were then returned to cages with conventional diet (standard rodent chow) and were monitored for survival. Results are set forth in Table 6 below wherein "Days to Death" indicates survival in days after tumor implantation.

TABLE 6

| Treatment | Days to Death | Median Days to Death | Number of Mice Surviving Beyond Control Range |
|---|---|---|---|
| None (Control) | 19,19,21,23,24,24 25,27,29,29 | 24 | |
| Melphalan alone | 20,20,27,27,36,36 41,41,42,42 | 36 | 6 |
| Melphalan + diet | 17,20,23,26,33,36 37,42,46,47 | 34 | 6 |
| Melphalan + LOX | 19,21,22,30,30,30 30,33,36,38 | 30 | 7 |
| Melphalan + diet + LOX | 19,19,19,36,36,44 44,44,46,47 | 40 | 7 |

The results shown in Table 6 indicate that tumor bearing animals receiving no treatment died between 19 and 29 days following tumor implantation with a mean survival of 24 days. Melphalan alone increased survival in some but not all animals; mean survival increased to 36 days. Six of the 10 treated animals had survival times greater than any of the animals receiving no treatment. Some but not all animals receiving melphalan after fasting and exposure to a protein-free diet showed increased survival relative to animals receiving no treatment; mean survival was 34 days. Six of the 10 animals in this group had survival times greater than any of the animals receiving no treatment. Two of the animals had survival times exceeding those observed in the group of animals receiving melphalan alone. Some but not all animals receiving melphalan+L-amino acid oxidase exhibited survival times greater than the range of survival times observed in the animals receiving no treatment; mean survival was 30 days. Seven of 10 animals in this group had survival times greater than any of the animals receiving no treatment. Some but not all animals in the group receiving L-amino acid oxidase and given melphalan after a fast and protein-free diet exhibited survival times greater than those observed in the group receiving no treatment. Mean survival time was 40 days; a value greater than that observed with any other treatment group. Seven of the 10 animals exhibited survival times greater than any of the animals receiving no treatment. Five of the 10 animals exhibited survival times greater than any observed in the group receiving melphalan alone. Median survival time in the group receiving melphalan+dietary manipulation+L-amino acid oxidase was greater than median survival time in the group receiving melphalan+dietary manipulation alone.

Enzymes which may be substituted for L-amino acid oxidase in the method herein include amino acid decarboxylases directed at amino acids transported by the large neutral amino acid carrier, and phenylalanine ammonia lyase.

Drugs besides L-melphalan whose transport may be improved on use instead of melphalan in the method herein include sarcolysin (D,L-melphalan); melphalan (D-melphalan); meta-sarcolysin, which is 3-[m-(bis-(2'-chloroethyl)amino)]phenyl-D,L-alanine; and amino-chlorambucil, which is a higher homolog of melphalan; and in general nitrogen mustards of any of the large neutral amino acids mentioned herein, or any anticancer drug transported by the large neutral amino acid carrier which has a specificity for large neutral alpha-amino acids.

Many variations of inventive embodiments will be obvious to those skilled in the art. Thus, the inventive embodiments are defined by the claims.

What is claimed is:

1. A method of treating a patient for tumors susceptible to melphalan, comprising:
   (a) administering L-amino acid oxidase to said patient at a dosage ranging from about 1 to about 100 units/ml of plasma, which is non-toxic and which is sufficient to reduce the plasma level of large neutral amino acids from a normal level to a melphalan transport improving level;
   (b) administering an anti-tumor effective amount of melphalan to said patient within about 2 to 36 hours after administering L-amino acid oxidase, wherein the plasma level of large neural amino acids has been reduced.

2. The method of claim 1, wherein the dosage of L-amino acid oxidase administered in step (a) ranges from about 10 to about 50 units/ml of plasma.

3. The method of claim 1 wherein the administration of step (b) is carried out from 12 to 30 hours after the administration of step (a).

4. The method of claim 1 further comprising, between the administering of step (a) and the administering of step (b), preventing replenishment of large neutral amino acids to plasma.

5. The method of claim 4 wherein preventing replenishment comprises causing the patient to fast.

6. The method of claim 4 wherein preventing replenishment comprises administering to said patient a protein-free diet.

7. The method of claim 5 wherein preventing replenishment comprises causing the patient to fast followed by administering a protein-free diet to the patient.

8. The method of claim 1 wherein the tumors are gliomas.

* * * * *